US00PP34205P2

(12) United States Plant Patent
Hansen

(10) Patent No.: US PP34,205 P2
(45) Date of Patent: May 3, 2022

(54) ***MONARDA* PLANT NAMED 'LEADING LADY PINK'**

(50) Latin Name: ***Monarda* hybrid**
Varietal Denomination: Leading Lady Pink

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,861

(22) Filed: Nov. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell

(57) ABSTRACT

The new and distinct cultivar of ornamental cultivar of hybrid ornamental Bee Balm plant named *Monarda* 'Leading Lady Pink' with deep-green, moderately-glossy, powdery mildew-tolerant foliage, dense flower heads of bright-pink flowers with lighter interiors effectively showing off the darker purplish-red spots. The plant habit is compact and winter-hardy, useful in the landscape as a specimen, en masse, or as a containerized plant.

1 Drawing Sheet

Botanical classification: *Monarda* hybrid.
Variety denomination: 'Leading Lady Pink'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 12, 2021. Prior to that, on Dec. 1, 2020 the claimed plant was displayed with a non-enabling photograph and brief description in a website operated by Walters Gardens, Inc., and on May 21, 2021 as a non-enabling photograph and brief description in the 2021-2022 Catalog by Walters Gardens, Inc., who obtained the plant and all information relating thereto, from the inventor. The first sales of the new plant were on May 31, 2021 by Walters Gardens, Inc. to Andrew's Greenhouse. No plants of *Monarda* 'Leading Lady Pink' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Leading Lady Pink', and hereinafter also referred to solely by the cultivar 'Leading Lady Pink' or the "new plant." *Monarda* 'Leading Lady Pink' was the result of a controlled pollination in the summer of Jul. 24, 2014 in a trial garden at a wholesale perennial nursery in Zeeland, Mich., USA. The female parent is a proprietary, unnamed, unreleased hybrid known as 12-27-1 (not patented) and the specific male parent is a proprietary, unnamed, unreleased hybrid known as 12-62-25 (not patented). The new plant was separated out for further evaluation in the summer of 2016 in the full sun trial gardens of the same nursery and assigned the breeder code 14-15-1. The new plant is the result of a planned breeding program of the inventor to produce new colors of flowers with increased mildew resistance and improved compact habit. The new plant has been asexually propagated since 2016 by division and by basal stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Leading Lady Pink' is unique from its parents and all other Bee Balm plants known to the inventor. The nearest comparison cultivars known to the inventor are 'Bubblegum Blast' U.S. Plant Pat. No. 27,497, 'Electric Neon Pink' U.S. Plant Pat. No. 30,347, 'Leading Lady Orchid' U.S. Plant Pat. No. 33,132 and 'Berry Taffy' U.S. Plant patent application Ser. No. 17/300,434, and 'Leading Lady Razzberry' co-pending U.S. Plant patent application Ser. No. 17/300,860.

'Bubblegum Blast' has lighter hot pink flowers and the habit is taller. 'Electric Neon Pink' has flowers of a dark neon-pink color and is significantly taller in habit. 'Berry Taffy' has a similar height and a little narrower in width, but the flower color is hot raspberry pink and lacks the dark spots on the petals. 'Leading Lady Pink' flowers earlier than all the above listed comparison cultivars. 'Leading Lady Orchid' has corolla tubes with an orchid-pink color and the outer petal is light pink. 'Leading Lady Razzberry' has a similar habit and flowering period, but the flowers are bright, raspberry-purple with darker purplish-red dots.

The female parent is more open and taller in habit than the new plant with lighter green foliage and flowers of rose-red color. The male parent flowers later in the season and the flowers are more purple without spotting.

*Monarda* 'Leading Lady Pink' is distinct from all Bee Balm plants known to the inventor. The following are traits of the new plant that in combination distinguish it from all other Bee Balm known to the inventor:

1. Deep-green, moderately-glossy, powdery mildew-tolerant foliage;
2. Short, compact, clumping, upright mound that is winter-hardy habit;
3. Compact, bright-pink flowers with lighter interiors effectively show off the darker purplish-red spots;
4. Flowering over a five-week-long period beginning early June;
5. Flowering in dense verticils.

BRIEF DESCRIPTION OF THE DRAWINGS

The photographs of the new plant demonstrate the unique traits of *Monarda* 'Leading Lady Pink' and the overall appearance of the plant at three-years-old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
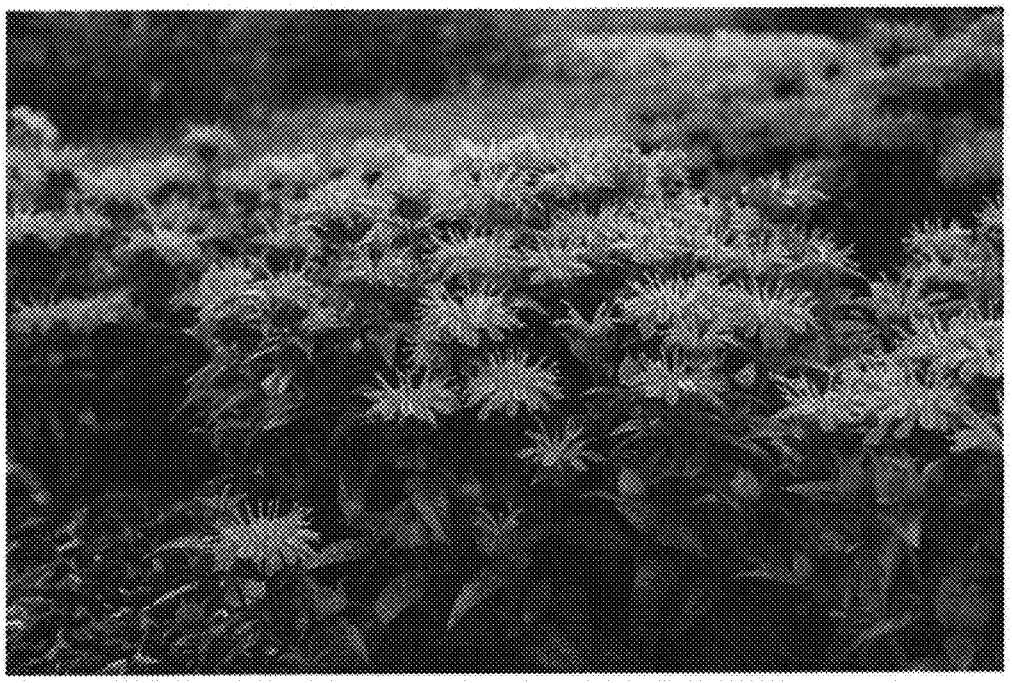
FIG. 1 shows the habit of the new plant in full flower.
Figure 2:
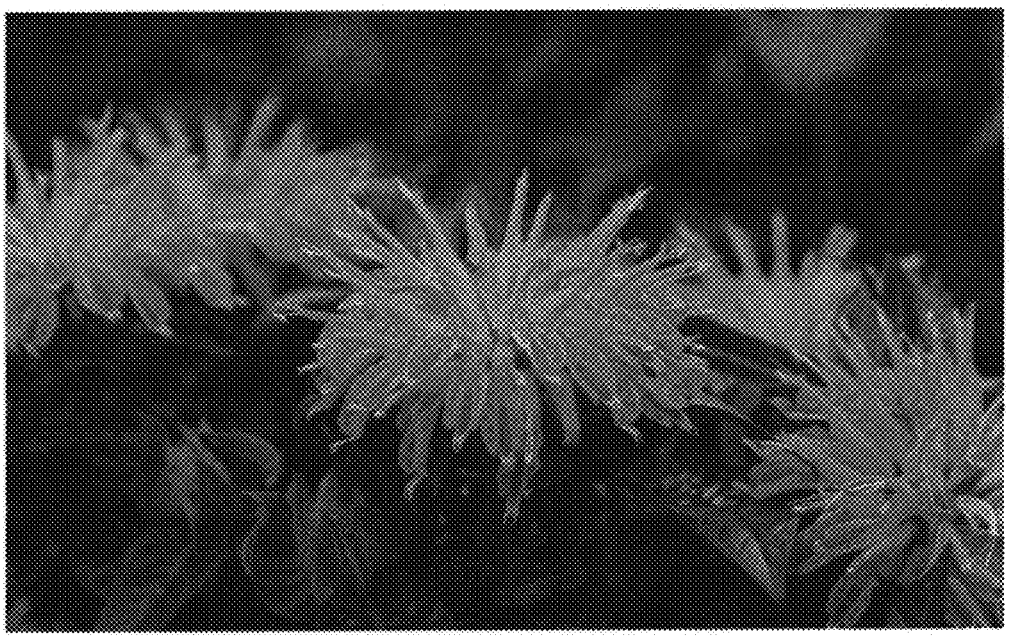
FIG. 2 shows a close-up of the flower of the new plant.

The following descriptions and color references are based on the 2015 edition of The Royal Horticultural Society Colour Chart except where common dictionary terms are used. *Monarda* 'Leading Lady Pink' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a trial garden at a nursery in Zeeland, Mich. with supplemental fertilizer and water as needed. Botanical classification: *Monarda* hybrid;

Parentage: The female (seed) parent is 12-27-1, an unreleased proprietary hybrid; the male (pollen) parent is 12-62-25, an unreleased, proprietary hybrid;

Plant habit: Hardy herbaceous perennial, dense, upright mound, producing multiple stems spreading by short rhizomes near the base of the stems; foliage up to 30.0 cm tall, flowering to 35.0 cm tall and 58.0 cm wide; flowering begins late spring in Michigan and continues for about 5 weeks;

Propagation: Stem cuttings;

Time to produce finished crop in 3.8-liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; moderately lustrous adaxial, matte to slightly lustrous abaxial; narrowly acute apex; cordate to rounded base; to about 8.7 cm long and 3.8 cm wide, average about 6.8 cm long and 3.3 cm wide near base;

Leaf color: Young expanding leaves adaxial nearest RHS 137A, abaxial nearest RHS 146B; older leaves adaxial nearest RHS 147C without significant anthocyanins, abaxial nearest RHS 147B without significant anthocyanins;

Foliage fragrance: Pleasant lemony-herbal;

Veins: Pinnate; glabrous and slightly sunken adaxial, micro-pubescent and costate abaxial;

Vein color: Adaxial midrib nearest RHS 145C and lateral pinnate veins and secondary veins RHS 145B near center and distally nearest RHS 138B; abaxial midrib variable, nearest RHS 145C and lateral pinnate veins nearest RHS 147C and secondary veins nearest RHS 137B;

Petiole: Micro-puberulent, slightly concaved above; to about 5.0 mm long and 3.0 mm across at base;

Petiole color: Adaxial nearest RHS 146C and abaxial nearest RHS 146D without significant anthocyanin;

Stems: Quadrangular; puberulent; about 4.0 mm across at base; about 40 per plant; naturally branched at upper nodes; average 2.7 cm between nodes, greater distally; 9 to 11 nodes per stem; average length about 30 cm;

Stem color: Nearest RHS 146D without anthocyanin expression; nodes same color as surrounding stem;

Flowers: Single, bilabiate flowers arranged in mostly terminal verticils forming globular head inflorescence about 70.0 mm across and 40.0 mm tall, opening from the center and progressing outwardly and down; attitude outwardly to upwardly; individual flowers to about 37.0 mm long to exserted stigma, 15.0 mm tall and about 5.0 mm across; individual flowers persisting about 5 days in Michigan; numerous, about 150 to 200 flowers per terminal head, fewer per axillary head; 60 inflorescences with open flowers at one time;

Flower fragrance: Moderately spicy;

Buds one to two days prior to opening: Narrowly oblanceolate, arcuate downward; about 21.0 mm long and 3.0 mm across and 5.5 mm tall;

Bud color: Basal 4.0 mm nearest RHS NN155B, distal and dorsal portion between RHS 61B and RHS 64B ventral region between RHS 61A and RHS 61B;

Petals: Bilabiate; arcuate downward; basal 18.0 mm fused into tube; split in two in the distal 15.0 mm; abaxial glandular to puberulent, adaxial glabrous; self-cleaning;

Upper labium: Rolled or folded in middle portion, about 12.0 mm long from fusion to acute apex, 2.0 mm tall, 2.0 mm across at base;

Lower labium: About 15.0 mm long from fusion to apex, apex comprising three lobes including two side lobes about 1.0 mm long and 2.0 mm across with rounded apex; center lobe bent upwardly at base, about 4.0 mm long with emarginate apex in the distal 0.5 mm; main portion with darker spots between 0.2 mm and 1.0 mm across;

Petal color: Upper labium adaxial surface nearest RHS 63B, abaxial between RHS 61B and RHS 64B; lower labium adaxial surface between RHS 61C and RHS 64C spots nearest RHS 61A, abaxial nearest RHS 63B with spots showing through from adaxial surface of nearest RHS 64A; corolla adaxial tube proximal 5.0 mm nearest RHS NN155C and distally nearest RHS 65B, abaxial tube proximal 5.0 mm between RHS 157D and RHS NN155B and dorsal distal portion nearest RHS 63B and ventral distal portion nearest RHS 64D;

Androecium: Two; adnate inner corolla tube in basal portion;

*Filaments.*—Two; curved downward; adnate to the inner corolla tube in the basal 15.0 mm and free in the distal 15.0 mm; about 0.5 mm diameter; color in free portion between RHS 68B and RHS 68C, color in adnate portion nearest RHS 69B.

*Anther.*—Oblong elliptic; dorsifixed; longitudinal; fused together; 3.0 mm long by 1.0 mm wide; color nearest RHS 62D and ventral suture color nearest RHS 187D.

*Pollen.*—Abundant, elliptic to globose, less than 0.1 mm; color nearest RHS 16A.

Gynoecium: One; superior; about 32.0 mm long;

Pistil: One per flower; exserted about 5.0 mm beyond upper labium when mature;

Style: Cylindrical; glabrous; about 29.0 mm long and about 0.3 mm diameter; arcuate along upper labium; color nearest RHS 64B in distal 5.0 mm transitioning to nearest RHS NN155D in middle and basal portion;

Stigma: Unevenly bifid in the distal 1.0 mm with one portion 1.0 mm and the other 0.5 mm long, about 0.2 mm in diameter; color nearest RHS 64A;

Ovary: Conical; about 1.0 mm tall by 0.75 mm diameter; color nearest RHS 145D;

Calyx: Tubular to campanulate; consisting of five fused sepals; about 8.0 mm long and 2.0 mm diameter at apex;

Sepals: Five; narrowly acute apex; basal 7.0 mm fused forming calyx tube, free in distal 1.0 mm; margin micro-serrulate; about 8.0 mm long and 1.0 mm across at fusion; glabrous abaxial, glabrous adaxial except throat pubescent; persistent;

Sepal color: adaxial and abaxial basal 2.0 mm nearest RHS 145D, middle adaxial portion nearest RHS 145B with veins nearest RHS 146C, middle abaxial portion nearest RHS 146D with veins nearest RHS 146C; adaxial and abaxial margins nearest RHS N187A;

Foliar bracts: Typically two sets of five to seven large bracts below inflorescence; proximal set deltoid, distal set lanceolate; apex narrowly acute; base sessile and truncate; margin entire and micro-ciliolate; glabrous adaxial, puberulent abaxial; mostly flat; proximal set about 18.0 mm long and 14.0 mm wide, distal set about 14.0 mm long and 4.0 mm wide;

Foliar bract color: Both sets similar, adaxial and abaxial nearest RHS 137A with occasional center of nearest RHS N186D;

Peduncle: Pubescent, stiff, strong, erect, quadrangular; to about 3.0 mm across above leaves and average 38.0 mm long above node; about 60 per plant at one time; naturally branched at nodes;

Peduncle color: Variable between RHS 146B and RHS 146A;

Pedicel: About 2.0 mm long and 0.8 mm diameter; color nearest RHS 145B;

Fruit: Single, glabrous, lustrous, ellipsoidal nutlet; about 1.2 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side-by-side comparison with other *Monarda*.

I claim:

1. A new and distinct hybrid ornamental Bee Balm plant named *Monarda* 'Leading Lady Pink', as herein described and illustrated.

* * * * *